April 25, 1950 W. B. CLARKE Plant Pat. 937
LILAC PLANT
Filed Sept. 30 1948
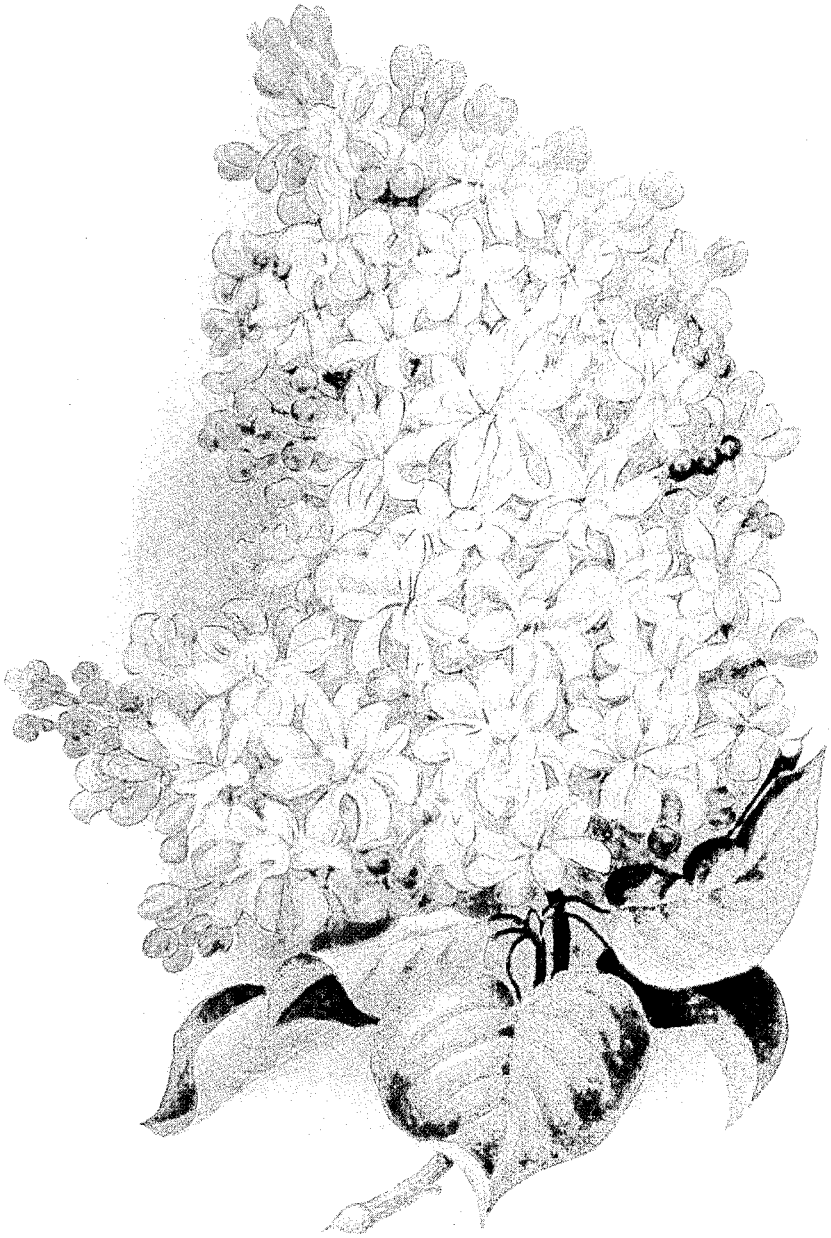
WITNESS
Addison E. Avery
INVENTOR
WALTER BOSWORTH CLARKE,
by Kuoonler Kuoonler & Snow,
ATTYS.

Patented Apr. 25, 1950

Plant Pat. 937

UNITED STATES PATENT OFFICE

937

LILAC PLANT

Walter Bosworth Clarke, San Jose, Calif., assignor to W. B. Clarke & Co., San Jose, Calif., a partnership Application September 30, 1948, Serial No. 52,031

1 Claim. (Cl. 47—60)

The hereindescribed lilac plant originated at San Jose, county of Santa Clara, California, as a seedling of an unnamed double.

This plant was discovered and tagged for observation on April 28, 1941, and has since been reproduced asexually by budding, and its distinctive characteristics are identical in the resulting plants.

In general appearance, except for its distinctive coloring and the appearance of its blooms, it resembles other varieties of *Syringa vulgaris*.

This plant is a new and distinct double-flowered variety and is the result of definite breeding efforts to produce a distinctive variety with red flowers close to the primary red hue. The present variety approaches the primary red more closely than any other lilac known to me.

In the accompanying painting a single flower cluster is shown, but it is to be understood that in the actual plant, the stems are forked and bear the flower clusters in pairs. These clusters are usually rounded at the tip and rather broad for their length.

The individual florets are unusually large, attaining a maximum width of about one and one-quarter inches (1¼″). In color the buds are a deep mauve carmine and the open flowers are a ruddy purple. A distinctive feature of the plant is that the individual florets are not crowded in the cluster. When the cluster is half open there is a striking contrast between the deep carmine of the buds and the bright red purple of the large open flowers. The petals (corolla lobes) are distinguished by being rather long and narrow. The clusters are of moderate size and very freely produced on the plant.

A more definite identification of this variety's distinctive coloring is given in the following table, having reference to the Horticultural Colour Chart issued by The British Colour Council in collaboration with The Royal Horticultural Society of London, England, copyright by Robert F. Wilson, 1938:

| | Color | Plate | Vol. | No. |
|---|---|---|---|---|
| Flower: General tone of flower shading out from center through to light outer edges. | Solferino Purple | 26<br>26<br>26 | 1<br>1<br>1 | 26/1<br>26/2<br>26/3 |
| Buds | | 26 | 1 | 26 |
| Leaf | Scheeles Green | 175 | 2 | 860/2 |

I claim:

The new variety of *Syringa vulgaris* plant, substantially as described and illustrated, characterized by the size and distinctive red purple color of its blooms and the uncrowded distribution of its florets in the cluster.

WALTER BOSWORTH CLARKE.

No references cited.